United States Patent [19]

Townsend

[11] Patent Number: 4,945,575

[45] Date of Patent: Aug. 7, 1990

[54] SUN VISOR

[76] Inventor: Charles E. Townsend, One Market Plaza, 20th Floor, San Francisco, Calif. 94105

[21] Appl. No.: 244,873

[22] Filed: Sep. 15, 1988

[51] Int. Cl.⁵ .............................................. A42B 1/18
[52] U.S. Cl. .................................................. 2/12; 2/177
[58] Field of Search .................... 2/12, 177, 200, 195, 2/175, 10, 209.7, 209.3, 184.5, 171.1

[56] References Cited

U.S. PATENT DOCUMENTS 3,927,421 12/1975 Simon ........................................ 2/12
4,292,689 10/1981 Townsend, Jr. ...................... 2/177 X
4,476,589 10/1984 Burgin ................................... 2/177 X

FOREIGN PATENT DOCUMENTS 1087393 8/1954 France ....................................... 2/12

Primary Examiner—Peter Nerbun
Attorney, Agent, or Firm—Charles E. Townsend, Jr.

[57] ABSTRACT

A sun visor is disclosed having a plurality of louvers of differing vertical heights with the innermost louver being the highest in elevation to thereby provide overhead light cutoff angles that shield the wearer's eyes from direct rays of the sun.

12 Claims, 2 Drawing Sheets

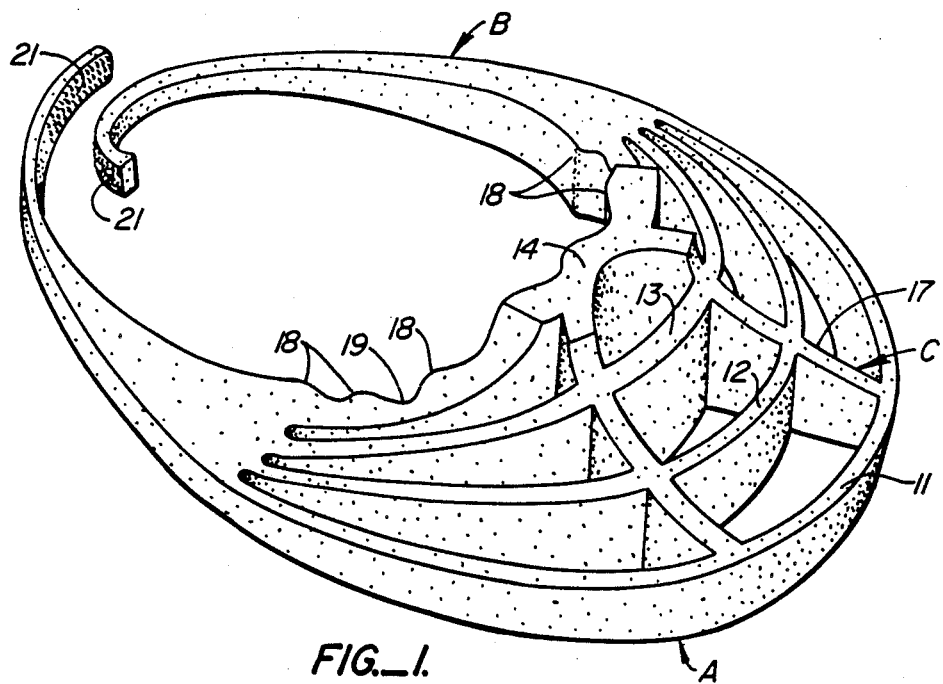
FIG._1.
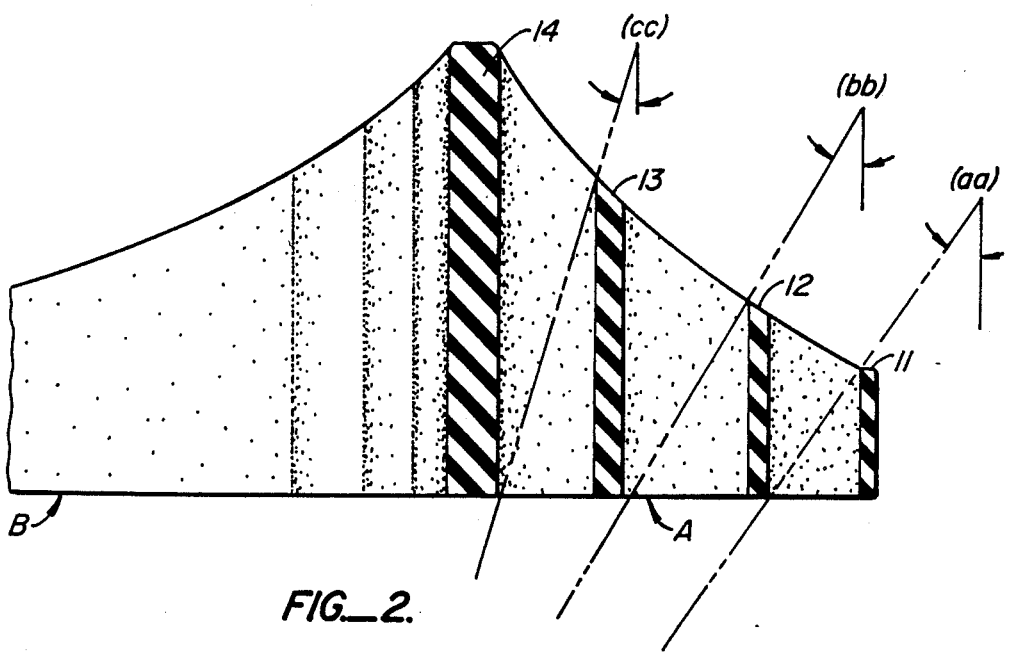
FIG._2.

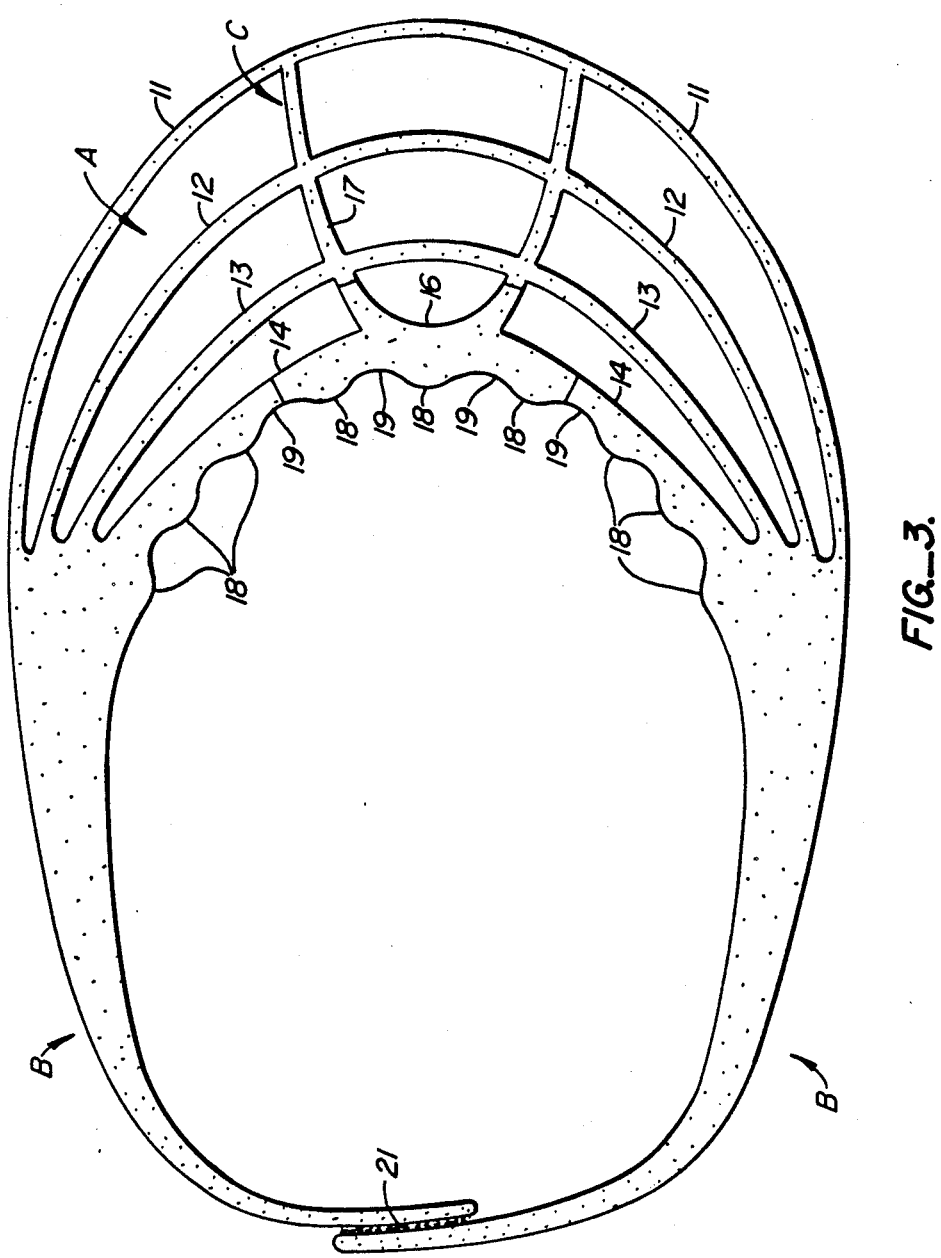

SUN VISOR

BACKGROUND OF THE INVENTION

1. Field of the Invention

This invention relates to a new and improved sun visor.

2. Description of the Relevant Art

Heretofore, it has been known to provide eye shades or sun visors in which the outwardly projecting bill is formed to include vertical or vertically tilted horizontally spaced louvers to provide venetian-blind type of light cut-off angles to prevent direct overhead rays of the sun from directly shining into the eyes of a user. In my prior U.S. Pat. No. 4,292,689 dated Oct. 6, 1981, there is shown and described a number of embodiments of such a class of sun visors. Generally speaking, louver-type bills in prior art structures are usually formed or fabricated from a single substantially flat piece of material and of generally uniform thickness. Although some such prior art visors provide reasonably satisfactory results, the cantilevered bills are often times structurally flimsy and because of their flat appearing front and side profiles, the bills are not aesthetically attractive.

SUMMARY OF THE INVENTION

An object of the present invention is to provide a sun visor incorporating an outwardly extending bill portion which comprises a plurality of curvilinear substantially vertically disposed ribbon-like louvers symetrically arranged and spaced from one another so as to include an outer louver, at least one intermediate louver and an innermost louver. The plurality of louvers are of differing vertical heights with the longest outer louver being the lowest in vertical elevation, the innermost louver being the highest in elevation, and the intermediate louver or louvers being higher in vertical elevation in the outer louver and less than vertical elevation than the innermost louver. The relative heights and maximum spacing between the louvers are predetermined and arranged to provide overhead like cut-off angles to shield the wearer's eyes from direct rays from the Sun. Further, the ribbon like louvers are made relatively thin, and this fact coupled with the relatively wide and open spacing between louvers, permits the bill to be made so that 90%, more or less, of the bill is open air presenting comparatively little underside wind load area that would otherwise cause the visor to blow off a user's head in only moderately gusty winds. A commonly experienced inconvenience and disadvantage of conventional solid bill visors is their tendency to blow off in only modest breezes, which requires a user to tighten the adjustable headband creating a kind of tourniquet feeling which most persons find uncomfortable and unpleasant.

Means, including an adjustable headband to encircle a user's head in a comfortable fit enables the user to position the visor on his head in conventional fashion so that the bill projects outwardly over his eyes to provide the desired sun shield.

In the preferred embodiment, the bottom edges of all the louvers are disposed in a common horizontal plane whereby when the visor is in normal position on a wearer's head, there is no arch or bow to the bill to obstruct the wearer's peripheral or lateral vision. The resulting sensation is that once the visor is in place, the wearer, looking straight ahead or to either side, is virtually visibly unaware that he is wearing any kind of outwardly projecting sun shade.

The progressive rise in elevations of the louvers from the outer louver upwardly toward the inner peak not only provides an aesthetically pleasing sculpted piece of head wear, but the louvers of graduated height increases the strength/weight ratio of the foam structure to provide a much more structurally stabilized bill than more conventional visors formed from more or less flat sheets of lightweight and inherently flimsy material.

Another object of the invention is to provide a visor incorporating the features above described that can be fabricated from extraordinarily lightweight and soft textured material such as low density foamed plastic materials, such as foamed polyethylene or foamed polyurethane. Although I have found there are numerous reasons why the apparent majority of people do not like the "feel" of wearing any kind of sports hat (such as conventional sports visors), one of the reasons is their sensing or feeling the weight and tourniquet binding around one's head of any conventional plastic or cloth visor. A visor embodying the present invention may be formed from foamed polyethylene of about 2 pound per square foot density or preferably form a foamed polyurethane as lightweight as approximately 1.7 pounds density. The entire visor including the louvered bill and the adjustable headband can all be made out of a single monolithic piece of this lightweight foam material so that a user when he adjustably positions the visor on his head in a loose fit (which is permitted by this particular design), virtually becomes physically unconscious of wearing any head gear largely because of the combination of the extraordinary light weight of the article, the lack of tightness of the headband, and, as above mentioned, the absence at the underside of any bowed or arched bill to obstruct the wearer's lateral or peripheral vision leading to his or her visible unawareness of wearing any kind of sun shade.

Another object of the invention is to provide a visor having generally the structural characteristics in design hereinabove described that is preferably fabricated entirely, or substantially entirely out of a lightweight foamed plastic, such as a 1.7 cubic foot density or of foam polyurethane that has the ability to almost immediately reform itself into its original shape after being intentionally or accidentally crushed or manipulated out of shape. An inherent disadvantage of most conventional visors of which I have knowledge, whether they be made out of plastic, cloth, cardboard or the like is that if they are subjected to crushing forces of sufficient magnitude to bend them out of shape, they have insufficient plastic memory to return themselves to their fully undeformed original configuration. In some instances, and depending upon the material, a user may be able to hand manipulate the crushed article to generally its original size, but with other materials such as stiff plastics or cardboard, the material can actually be flexed or ruptured to a point where it cannot be returned to its original shape, and must be discarded.

Another object, in a preferred embodiment, is to provide an entire visor, particularly the entire bill portion in the forehead contacting portion, which is made from a lightweight sponge water and perspiration absorbent material such as the aforementioned low density polyurethane foam material. The sinusoidal forehead contacting portion of a visor made with this material need not be provided with any separate cloth sweatband of the usual type as the entire structure will act to absorb perspiration from and around the forehead. In cases of extreme perspiration absorption, the user can simply wring out the perspiration so as not to increase the weight of the visor because of excessive moisture absorption. Further, at any time before, during or after use of the visor, the entire structure can be put under water and totally cleansed and squeezed out as would be the case with an ordinary kitchen sponge. In this connection, it is a simple task to maintain the entire visor free of perspiration stains or odors unlike conventional cloth visors which when they become unduly stained or odiferous, must be discarded because of their lack of convenient launderability. The present visor, if made of sponge material, can be easily washed and cleansed as many times as desired without affecting the structural integrity or longevity of the article.

Other numerous objects and advantages of the present invention will become apparent upon reading the following detailed specification and referring to the accompanying drawings in which corresponding parts are numbered similarly in each of the several views.

BRIEF DESCRIPTION OF THE DRAWINGS

In the drawings, FIG. 1 is a perspective view of a visor embodying the present invention.

FIG. 2 is a side elevational view of same.

FIG. 3 is a top plan view of same.

DETAILED DESCRIPTION OF THE EMBODIMENTS

Referring now particularly to the drawings, there is shown a monolithic visor which is formed from a single block of foam plastic material such as, preferably, a low density foamed polyurethane material.

Referring to FIGS. 1 and 3, especially, the complete visor therein shown may be deemed as comprising a bill portion indicated generally at A and a headband portion indicated generally at B. The bill portion A comprises a plurality of curvilinear substantially vertically disposed ribbon-like louvers including an outer louver 11, a first intermediate louver 12, a second intermediate louver 13 and a innermost louver 14. As FIG. 1 shows, the vertical height of the louvers are graduated from lowest to highest with the outermost louver 11 being the lowest in elevation and the innermost louver 14 being the highest. Innermost louver 14 rises to a point where it presents an arcuately peaked partial sun shield for the forehead of a wearer and is similar in its contour viewed from front elevation (FIG. 1) as in more conventional open-top visors.

The relative heights and spacing between the multiple louvers are predetermined and arranged to provide overhead light cutoff angles to shield the wearer's eyes from direct rays from the Sun. Referring to FIG. 1, the light cutoff angle between the top inner edge at centerpoint of the outer ribbon 11 and the outer bottom edge at centerpoint of louver 12 is indicated by the angle (aa). Similarly, the light cutoff angles between intermediate louvers 12 and 13 is indicated at (ab) and the light cutoff angle defined by the uppertop inner edge at centerpoint of louver 13 and the bottom outer edge at centerpoint of louver 14 is depicted at (ac). The largest light cutoff angle measured from vertical as depicted at (aa) is about 45 ©, although a light cutoff angle as large as 60 © can be tolerated without having direct rays of the Sun strike the user when the visor is positioned for normal wear on a user.

In order to fix and stabilize the spacing of the louvers relative to each other, there is provided a U-shaped ribbon structure (C) comprising more specifically a web portion 16, formed integral with the innermost ribbon 14 and defining outwardly extending legs 17 which integrally connect with and maintain the spacing between all of the louvers 11, 12 and 13.

The inner surface of the innermost louver and sun shield 14 is formed with vertical grooves resembling a sine wave and defining inwardly projecting nodes 18 and alternate depressions 19. The nodes 18 define spaced apart contact points so that when the visor is positioned on a wearer's head, his forehead will only be in intimate contact with the spaced nodal points to provide intermediate ventilation areas or grooves 19 and reduce the tendency of the visor to induce generation of perspiration as is the case with a continuous sweatband type of structure.

The headband B comprises integral rearward leg extensions from the bill portion A and the rearward terminal ends of the leg extensions may be overlapped and adjustably fastened by a conventional Velcro fastener 21 or the like to adjustably encircle and fit any normal head size.

In use, the extremely lightweight visor need not be fitted with the headband in tightened condition, even during moderately gusting winds in view of the minimum wind load resistance presented by the largely open air louvered bill. In short, a visor embodying the present invention has much less tendency to tend to blow off the head of a wearer even during moderately high gusting winds.

As earlier indicated, a visor of the configuration as shown in the drawings and herein described may be fabricated as a monolithic structure from a single block of low density foamed polyurethane material, such as for example a 1.7 lbs./cu./ft. density polyurethane foam having a measured compressive load deflection rating of around 90 ILD (indentation load deflection). The visor can be die-cut from a single rectangular block of such material using steel rule dies in conjunction with the so-called compression inversion technique known in the foam plastic industry. This known technique involves applying compressive forces to selected areas of a compressible foam block, and while such selected areas are under compression to straight cut or saw the block along predetermined lines so that when the cut off parts are permitted to recover from their compressed conditions, they "swell" and assume rounded or other predetermined shapes. In the instant case, before die-cutting the vertical shield 14 portion and other progressively elevated sections of the bill of the visor would be put under various and selected compression loads while the parent block of foam were band sawed in preselected parallel planes defining the flat underside of the visor and the top surfaces of the headband, for example. The open cell configuration of the visor as viewed in plan (FIG. 3) is the result of die-cutting the section cut from the parent block using the compression inversion technique.

It is also pointed out that a visor of basically the same design and configuration as herein shown and described may be fabricated from separately die cut ribbons of flat sheet material and simply bonded together at their contacting or merging points. Specifically, the louvers 11, 12, 13 and 14 initially may all be die-cut from flat sheets, then turned on edge and assembled and bonded together at the sides of the visor where all of these parts (including the legs of the headband) are shown as merging in the monolithic embodiment as shown.

Although the present invention has been described for purposes of clarity in some detail by way of illustration and example, it is understood that the breadth of the invention is limited only by the scope of the appended claims hereto.

What is claimed is:

1. An improved sun visor comprising an outwardly projecting bill portion, said bill portion comprising a plurality of curvilinear substantially vertically disposed ribbon-like louvers symetrically arranged and spaced from one another and including an outer louver, at least one intermediate louver, and in inner louver, said outer, intermediate and inner louvers having graduated predetermined vertical heights with the outer louver being the lowest in vertical elevation, the innermost louver, being the highest in elevation, and the intermediate louver being higher in vertical elevation that the outer louver and less in vertical elevation than the intermediate louver, the inner louver adjacent its center front portion being at least 20% greater in height than the height of the outer louver adjacent its center front portion, the relative heights and maximum spacing between the louvers being predetermined and arranged to provide overhead light cut-off angles to shield the wearer's eyes from direct rays of the sun, and means to attach the visor to a wearer's head with the bill projecting outwardly from the wearer's forehead above eye level.

2. The combination of claim 1 and wherein the bottom edges of the louvers are commonly disposed in a substantially horizontal flat plane.

3. The combination of claim 1 and wherein said outer, intermediate and inner louvers are joined together and stabilized by a least one vertically disposed reinforcing rib structure.

4. The combination of claim 3 and wherein the said reinforcing rib structure is U-shaped in plan defining side portions joined by a web portion and wherein the web portion of said U-shaped rib structure is joined to said inner louver, and the outwardly extending legs thereof are joined to the intermediate and outer louvers.

5. The combination of claim 1 and wherein the innermost louver extends upwardly to define a partial sun shield for a user's forehead, and wherein said sun shield viewed in front elevation is curved gradually downwardly in from a central peak elevation point toward and around to the sides of the visor.

6. The combination of claim 1 and wherein the innermost louver is provided with a sinusoidal forehead contacting portion.

7. The combination of claim 6 and wherein the sinusoidal forehead contacting portion is made of soft textured absorbent sponge-like material.

8. The combination of claim 1 and wherein the entire bill portion is formed as a monolithic structure from a single material.

9. The combination of claim 1 and wherein the material from which substantially the entire bill portion is formed comprises a lightweight foamed plastic.

10. The combination of claim 9 and wherein said foamed plastic is of an absorbent open cell sponge type.

11. The combination of claim 9 and wherein said foamed plastic is of a non-absorbent closed cell sponge type.

12. The combination of claim 9 and wherein said foamed plastic material is of a type characterized in having a relatively rapid and complete plastic memory recovery whereby when said bill portion is subject to physical crushing or deformation forces, the plastic memory of the cellular plastic material returns the structure to its original shape within a relatively short momentary time span.

* * * * *